United States Patent
Clements et al.

(10) Patent No.: US 7,674,346 B2
(45) Date of Patent: Mar. 9, 2010

(54) MULTI-WELL PLATE AND METHOD OF MANUFACTURE

(75) Inventors: James G. Clements, Brentwood, NH (US); Michael Curtis, Stratham, NH (US); Paul E. Gagnon, E. Farmington, NH (US); William J. Lacey, North Andover, MA (US); Gregory R. Martin, Acton, ME (US); David M. Root, Westford, MA (US); Allison J. Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 1545 days.

(21) Appl. No.: 10/966,856

(22) Filed: Oct. 15, 2004

(65) Prior Publication Data

US 2005/0047971 A1 Mar. 3, 2005

Related U.S. Application Data

(62) Division of application No. 09/837,241, filed on Apr. 18, 2001, now abandoned.

(60) Provisional application No. 60/198,604, filed on Apr. 19, 2000, provisional application No. 60/258,913, filed on Dec. 29, 2000.

(51) Int. Cl.
*B01L 3/00* (2006.01)

(52) U.S. Cl. .................. 156/272.2; 422/102; 156/273.3; 156/273.5

(58) Field of Classification Search .................. 422/102; 435/288.3, 288.4; 156/272.2, 273.2, 273.5, 156/273.7, 285, 311
See application file for complete search history.

(56) References Cited

U.S. PATENT DOCUMENTS

| | | | |
|---|---|---|---|
| 5,307,144 A | 4/1994 | Hiroshi et al. | 356/244 |
| 5,319,436 A | 6/1994 | Manns et al. | 356/246 |
| 5,342,581 A | 8/1994 | Sanadi | 422/101 |
| 5,487,872 A | 1/1996 | Hafeman et al. | 422/102 |
| 5,738,825 A | 4/1998 | Rudigier et al. | 422/82.11 |
| 5,853,894 A | 12/1998 | Brown | 428/422 |
| 5,910,287 A | 6/1999 | Cassin et al. | |
| 5,989,854 A | 11/1999 | Cook | 435/35 |
| 6,171,780 B1 * | 1/2001 | Pham et al. | 435/4 |
| 6,232,114 B1 | 5/2001 | Coassin et al. | 435/288.4 |
| 6,241,949 B1 | 6/2001 | Kane | 422/102 |
| RE38,214 E | 8/2003 | Lacey et al. | 422/102 |

FOREIGN PATENT DOCUMENTS

| | | |
|---|---|---|
| EP | 0571661 A1 | 1/1993 |
| EP | 0 844 025 | 5/1998 |
| EP | 1 586 379 | 6/2007 |
| WO | WO 95/16005 * | 6/1995 |
| WO | WO 98/55231 | 12/1998 |

* cited by examiner

*Primary Examiner*—Jill Warden
*Assistant Examiner*—Dwayne K Handy
(74) *Attorney, Agent, or Firm*—Susan S. Wilks

(57) ABSTRACT

A method of manufacture and assembly of multiwell plates employing targeted radiation at an interface in order to achieve bonding is disclosed. The method accommodates glass and polymer attachment as well as polymer to polymer attachment. Resultant plates have unique flatness and optical properties.

27 Claims, 15 Drawing Sheets

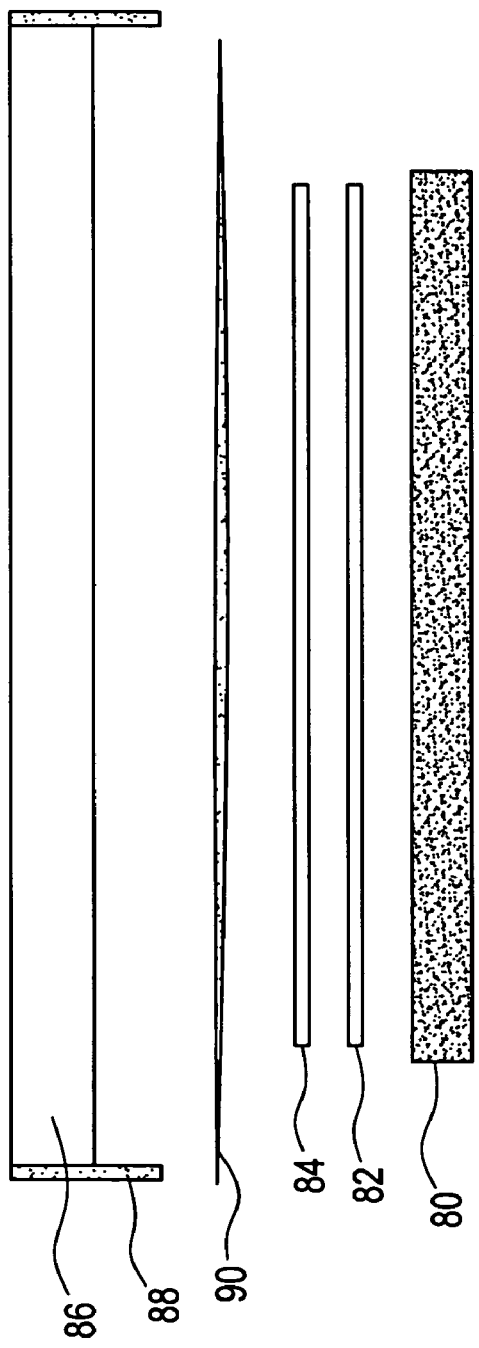
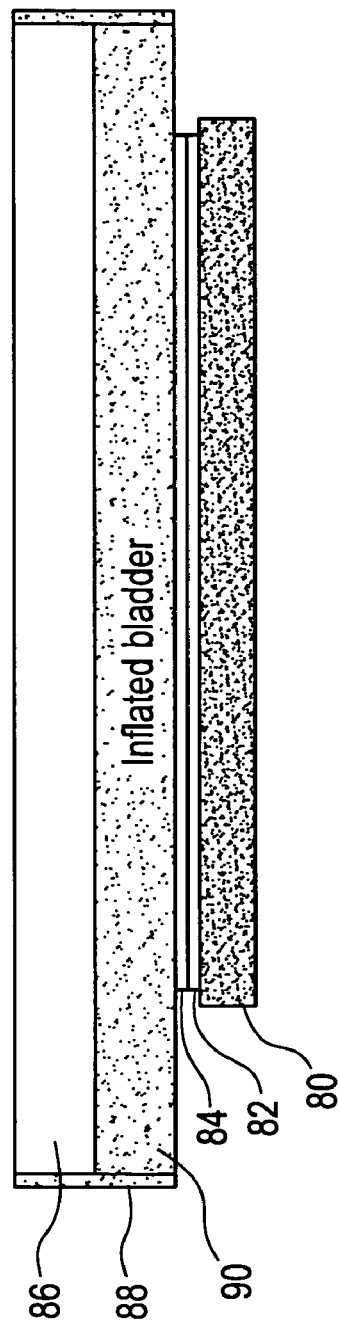
FIG. 9
FIG. 10

Within Well Flatness

US 7,674,346 B2

MULTI-WELL PLATE AND METHOD OF MANUFACTURE

CROSS REFERENCE TO RELATED APPLICATIONS

This application is a divisional of U.S. patent application Ser. No. 09/837,241, filed Apr. 18, 2001, now abandoned, which claims the benefit of U.S. Provisional Application No. 60/198,604, filed Apr. 19, 2000 and U.S. Provisional Application No. 60/258,913, filed Dec. 29, 2000. The benefit of priority under 35 U.S.C. 120 to the above referenced application is hereby claimed and the content of which is relied upon and incorporated by reference herein in its entirety.

FIELD OF INVENTION

The present invention relates generally to multiwell assay plates for use in chemical and biochemical analysis, and more particularly multiwell plates having transparent well bottoms and improved methods of manufacture.

BACKGROUND

The recent growth in many areas of biotechnology has increased the demand to perform a variety of studies, commonly referred to as assays, of biochemical systems. These assays include for example, biochemical reaction kinetics, DNA melting point determinations, DNA spectral shifts, DNA and protein concentration measurements, excitation/emission of fluorescent probes, enzyme activities, enzyme co-factor assays, homogeneous assays, drug metabolite assays, drug concentration assays, dispensing confirmation, volume confirmation, solvent concentration, and solvation concentration. Also, there are a number of assays which use intact living cells and which require visual examination.

Assays of biochemical systems are carried out on a large scale in both industry and academia, so it is desirable to have an apparatus that allows these assays to be performed in convenient and inexpensive fashion. Because they are relatively easy to handle, are low in cost, and generally disposable after a single use, multiwell plates are often used for such studies. Multiwell plates typically are formed from a polymeric material and consist of an ordered array of individual wells. Each well includes sidewalls and a bottom so that an aliquot of sample may be placed within each well. The wells may be arranged in a matrix of mutually perpendicular rows and columns. Common sizes for multiwell plates include matrices having dimensions of 8×12 (96 wells), 16×24 (384 wells), and 32×48 (1536 wells).

Typically, the materials used to construct a multiwell plate are selected based on the samples to be assayed and the analytical techniques to be used. For example, the materials of which the multiwell plate is made should be chemically inert to the components of the sample or any biological or chemical coating that has been applied to the plate. Further, the materials should be impervious to radiation or heating conditions to which the multiwell plate is exposed during the course of an experiment and should possess a sufficient rigidity for the application at hand.

In many applications, a transparent window in the bottom of each sample well is needed. Transparent bottoms are primarily used in assay techniques that rely on emission of light from a sample and subsequent spectroscopic measurements. Examples of such techniques include liquid scintillation counting, techniques which measure light emitted by luminescent labels, such as bioluminescent or chemoluminescent labels, fluorescent labels, or absorbance levels. Optically transparent bottom wells also lend the advantage of microscopic viewing of specimens and living cells within the well.

Currently, optically transparent and UV transparent bottomed multiwell plates exist in the market and are used for the purposes described. These plates typically are a hybrid of different polymeric materials, one material making up the well walls and another making up the bottom portion of the wells.

Ideally, plates to be used for spectroscopic and microscopic measurement would have well bottoms made from glass. Glass has the advantage of being chemically inert, has superior optical properties in the visible range, is rigid, and is highly resistant to any deformation process caused by heating, due to its high melting temperature. Further and unlike most polymers, glass can be formulated and processed to provide a surface which produces very little background signal and which may be manufactured to extreme smoothness. Still, its surface may be easily coated or otherwise altered in order to promote attachment of specific targeted molecules. For example, a silane coating may be applied to the glass in order to extend any variety of functional groups such as amine functionalities, for example. Such amine functionality may can be effectively used to immobilize reactive molecules of the types commonly used in biological assays and testing procedures, e.g., to immobilize specific binding members (e.g., antigens, ligands, and haptens), entire cells, proteins (e.g., binding proteins, receptor proteins, antibodies and antibody fragments), nucleic acids (e.g., RNA and DNA molecules), tissue and the like. Further, the use of a polylysine coating on glass cover slips to grow nerve cells is a standard procedure.

Unfortunately, while it is simple to make glass in sheets, it is not possible to injection mold articles made from glass, and it is extremely difficult to press a molten gob of glass into an industry standard assay plate format. One solution to the problem, offered by the present invention, is to combine an injection molded polymeric upper plate molded to form the wells of a microplate, with a substantially flat transparent glass lower plate to form the well bottoms. In order to accomplish this result, the inventors considered several known methods for combining glass and plastic. Two commonly employed methods of joining these types of materials are by means of adhesive bonding and by means of insert molding.

The use of adhesives to bond together the material forming the well bottoms and material forming the well walls is expensive and leads to contamination of the biologically sensitive well surface. Low molecular weight species from the polymeric material making up the sidewalls of the wells, as well as species within the adhesive itself, tend to migrate through the adhesive and onto the transparent bottom surface. When this occurs, biomolecules can not properly react with the surface as intended under particular assay conditions. Adhesives which are UV cured or UV stabilized also have the tendency to absorb UV light, which may result in altering fluorescent readings taken from a detector located above or below the plate. The effect of the UV light is to non-specifically modify the signal by non-specific fluorescence thus creating undesired background readings which are highly variable from well to well and from plate to plate.

Insert molding is another common technique for joining together polymeric and glass parts. In this manufacturing method, the polymer portion is molded against or around the glass portion. Since the polymer has a much lower melting temperature than the glass, the glass remains in solid form while the liquid polymer is pressed against it. Once hardened, the polymer/glass interface remains attached only by weak interactions. One way of increasing the mechanical strength of the connection is to mold around or encapsulate the glass with the polymer, e.g. in glass bottomed ashtrays. Unfortunately, using this technique to combine polymeric parts with glass sheets of microscope coverslip thickness, as described in multiwell plate manufacture, is not practical because the mechanical strength of glass at such thinness is extremely low.

SUMMARY

The present invention offers an improved multiwell plate and a method of making a multiwell plate having a transparent bottom welled portion which allows for undistorted spectroscopic measurement of light emissions from a sample. The method comprises the following steps: providing an upper plate having an array of open ended wells, the plate made from a polymeric material containing a silane and infrared absorbing particles and/or particles; providing a substantially flat glass sheet lower plate which is substantially transparent to infra red radiation at selected wavelengths; contacting the upper plate to the lower plate to form an interface; and, heating the upper plate at the interface above its transition temperature, through the lower plate, by means of infra-red radiation, the molten upper plate polymer wets the lower plate at the interface and the part is cooled such that the upper plate and the lower plate are bonded together by covalent attachment formed during the wetting, heating and cooling steps.

The present method allows for the attachment of flat glass of small thickness as the material for the transparent lower plate. Glass has the advantage that it will not polarize or stretch, and thereby will not distort the emission measurements obtained from the sample wells. In addition, glass may be manufactured to extreme optical flatness requirements and has a much higher melting temperature than the polymeric material making up the upper plate. As a result it is far less susceptible to any deformation from melting and is more likely to maintain its excellent optical properties.

The present method also allows for the attachment of like polymers (e.g. a polystyrene black opaque upper plate with an optically transparent polystyrene film), or attachment of unlike polymers (e.g. a polystyrene black opaque upper plate with a PTFE film). The resultant polymeric plates have unique characteristic flatness both across individual wells and across the entire plate.

BRIEF DESCRIPTION OF DRAWINGS

FIG. 9 is an exploded schematic cross sectional view of the assembly of parts in the manufacturing apparatus used in the present invention for producing a plate with a thin film bottom.

FIG. 10 is a schematic representation of the parts of FIG. 9 as assembled and clamped within the manufacturing apparatus.

DETAILED DESCRIPTION OF THE INVENTION

Figure 1:
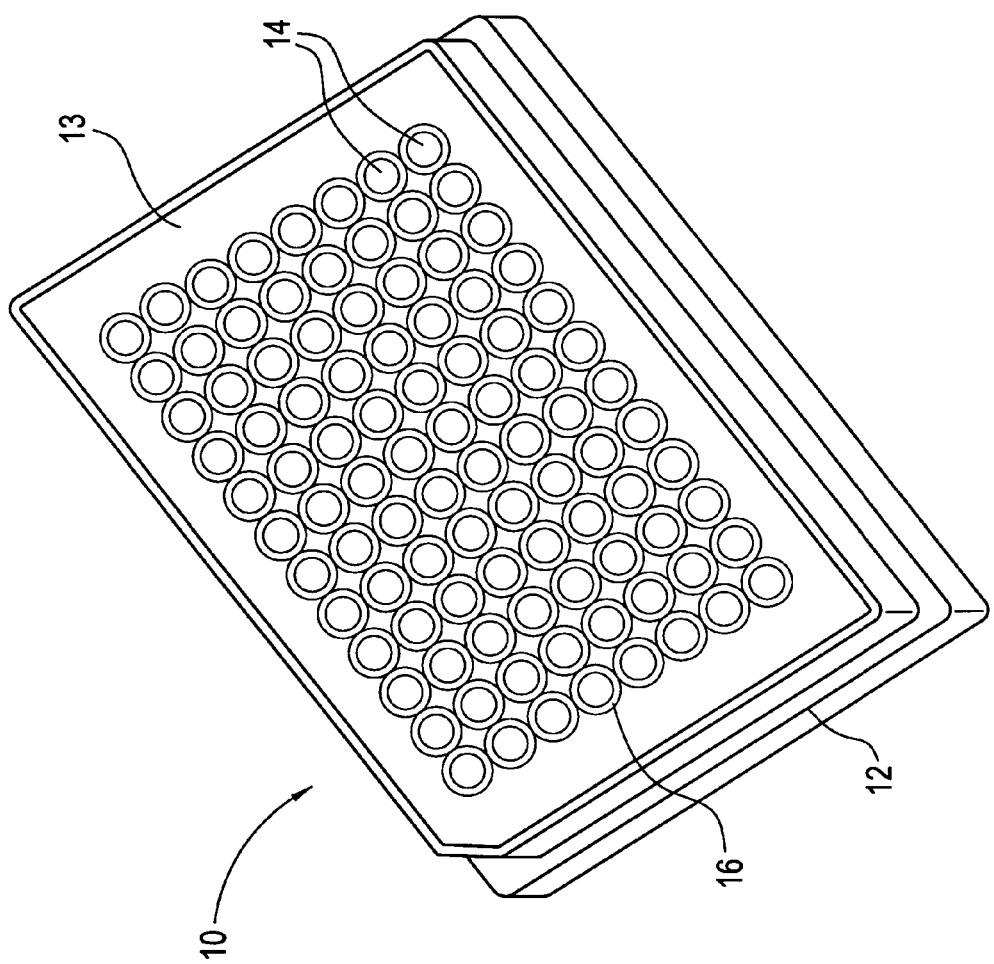
FIG. 1 is a three dimensional view of the multiwell plate of the present invention.

Shown in FIG. 1 is a multiwell test plate 10 of the present invention. The plate includes a peripheral skirt 12 and an upper surface 13 having an array of wells 14 each of which is capable of receiving an aliquot of sample to be assayed. Preferably, the plate conforms to industry standards for multiwell plates; that is to say, a plate bordered by a peripheral skirt 12, laid out with 96 wells in an 8×12 matrix (mutually perpendicular 8 and 12 well rows). In addition, the height, length, and width are preferably conform to industry standards. The present invention, however, can be implemented in any type of multiwell plate arrangement including 384 and 1536 wells, and is not limited to any specific number of wells or any specific dimensions.

Figure 2:
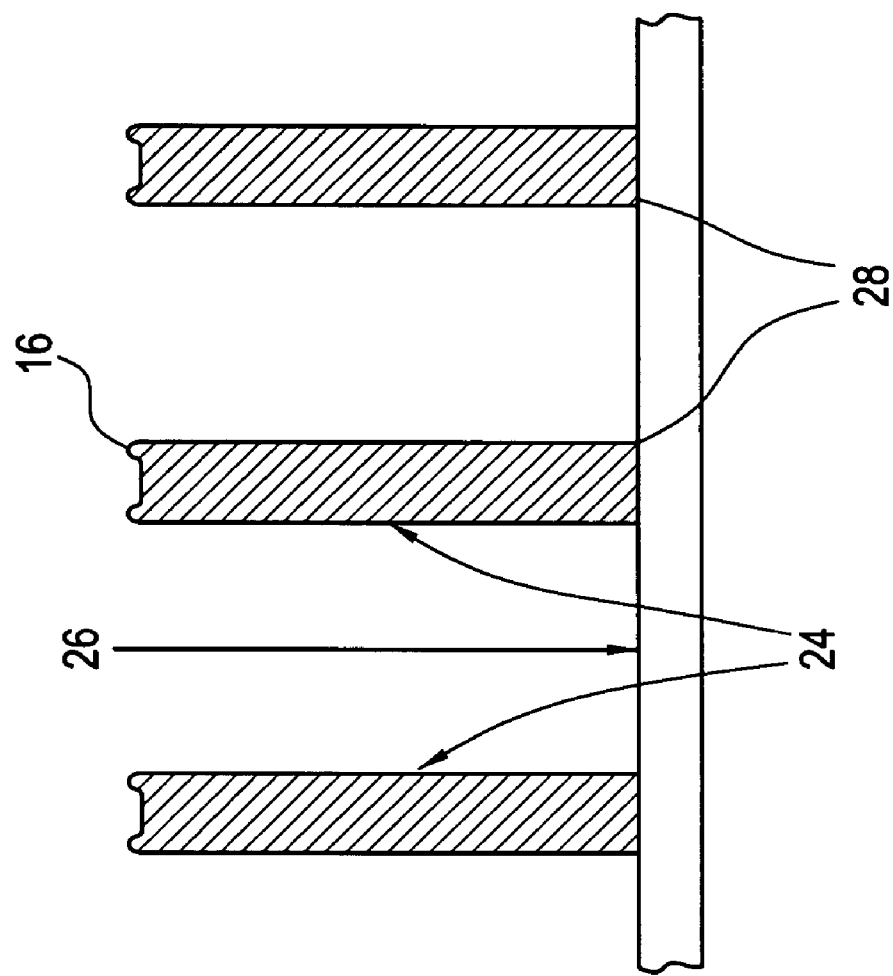
FIG. 2 is a partial cross section of the multiwell plate of the present invention. The upper and lower plates of the present invention are shown, after the two have been joined.

The plate is of two-part construction. Referring to FIG. 2, a partial cross section of multiwell plate 10, an upper plate 20 forms the well walls 24 and top surface; a lower plate 22 forms the well bottoms. During the manufacturing process as will be described in detail below, the two plates are integrally and chemically joined together at an interface 28.

Each well 14 includes a top rim 16, sidewalls 24, and a bottom 26. In order to prevent light transmission between adjacent wells, the sidewalls 24 are preferably formed from an opaque organic polymeric material or filled with an inorganic $TiO_2$ material. For assaying techniques which require the detection of very small amounts of light, as in liquid scintillation counting, the pigmentation used to render the polymeric material opaque is preferably light (e.g. white) in color so as to be highly reflective and non-absorptive in order to ensure high counting efficiency with respect to the radioactive samples. However the walls may be optically transparent. In some types of luminescence and fluorescence assays, it is preferred that the sidewalls 24 of the sample wells 14 be non-reflective and absorptive, in which case the well walls 24 are formed from a black pigmented polymer. As is commonly known and practiced, the black coloration of the polymer may be achieved by the addition of a pigment material such as carbon black to the polymer blend at concentrations readily known and practiced in the art. The white coloration is typically achieved with $TiO_2$.

The bottom of the wells 26, in contrast to the sidewalls 24, is formed from a transparent material. Preferably, the material is an inorganic such as glass, but may be pure silica, mica, or even metallic coated films. More preferably, the glass is of a high optical quality and flatness such as boroaluminosilicate glass (Corning Inc. Code 1737). Optical flatness of the well bottom and plate is important particularly when the plate is used for microscopic viewing of specimens and living cells within the wells. This flatness is important in providing even cell distribution and limiting optical variation. For example, if the well bottoms are domed, the cells will tend to pool in a ring around the outer portion of the well bottom. Conversely, if the wells are bowed downwards, the cells will pool at the lowest point. Glass microscope slides are typically flat within microns in order to ensure an even distribution. Preferably, the well bottoms are formed from a glass sheet having a thickness similar to microscope slide cover slips, which are manufactured to match the optics of a particular microscope lens. Although the well bottoms may be of any thickness, for microscopic viewing it is preferred that the well bottom thickness be in the range of 5-100 microns and have a flatness in the range of 0-10 microns across the diameter of the outer bottommost surface of an individual well. The inner and outer surfaces of these wells are coplanar.

The glass material used here can be purchased from a variety of manufacturers (e.g. Erie Scientific, Corning, Inc.) as a sheet. These sheets can then be altered to fit the dimensions of the desired size plate. This forms a transparent bottom wall 26 for each sample well 14 and permits viewing therethrough. The transparent lower plate also allows for light emissions to be measured through the bottom of the sample wells 14.

The multiwell plate 10 is comprised of two separate parts. A separately molded upper plate 20, comprising an array of open ended sample wells 14, is used to form the sidewalls 24, the peripheral skirt 12, and top surface 13. The upper plate is preferably molded from long polymers that become intertwined with heating and bond together in a noncovalent mechanism upon cooling, thereby forming an interpenetrating polymer network. Further, the upper plate preferably is chosen from a group of polymers containing a silane functionality. Silane functional polymer can be copolymerized with other monomers to create polymers with pendent silane groups. These polymers will crosslink upon exposure to moisture in the environment giving a toughened final polymer. An example of a suitable material is poly (ethylene-co-trialkoxyvinylsilane). The silane functionality in the polymer is important in creating a covalent attachment with the glass lower plate that is used to form the well bottoms 26. The two plates are brought into contact at an interface 28 where covalent attachments between the silane functionality of the organic polymeric material forming the upper plate 20 and the hydroxyl functionality of the glass lower plate 22 create the covalent attachment.

It should be noted that the upper plate need not be molded. For example, a sheet of the silane polymer may be provided into which wells are drilled out by laser, punched out, or otherwise extracted. Further, the upper plate may be laminated so that each layer has desired properties. For example, a top most layer may be anti-reflective, a middle layer forming the plate's sidewalls may be hydrophobic for meniscus control, an the bottommost layer which contact the glass lower plate is a silane polymer.

The wells 14 can be any volume or depth, but in accordance with the 96 well industry standard, the wells will have a volume of approximately 300 ul and a depth of 12 mm. Spacing between wells is approximately 9 mm between center lines of rows in the x and y directions. The overall height, width, and length dimensions of the plate are preferably standardized at 14 mm, 85 mm and 128 mm, respectively. Wells can be made in any cross sectional shape (in plan view) including, square, sheer vertical walls with flat or round bottoms, conical walls with flat or round bottoms, and combinations thereof.

Figure 3:
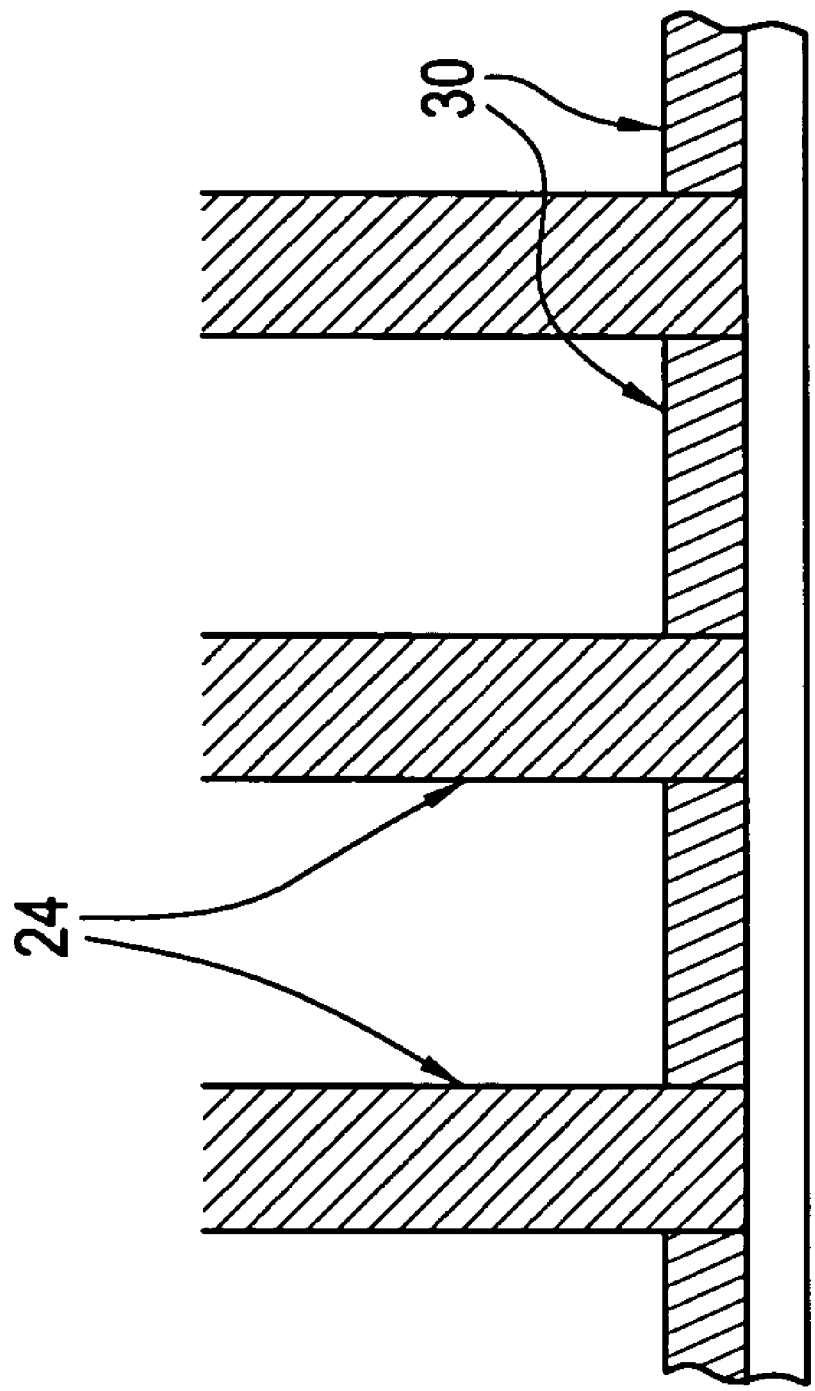
FIG. 3 is a partial cross section of an embodiment of the multiwell plate of the present invention, showing the bottom plate treated with a chemically active coating.

FIG. 3 shows a partial cross sectional view of one embodiment of the present invention. This figure, however, also shows a chemically active coating 30 that can be added onto the inner surface of the lower plate 22. Depending on the assay requirements, any number of chemically active coatings described in more detail below, may be used to treat the glass surface of the well bottoms, both on the inner and outer well bottom surfaces.

Figure 4:
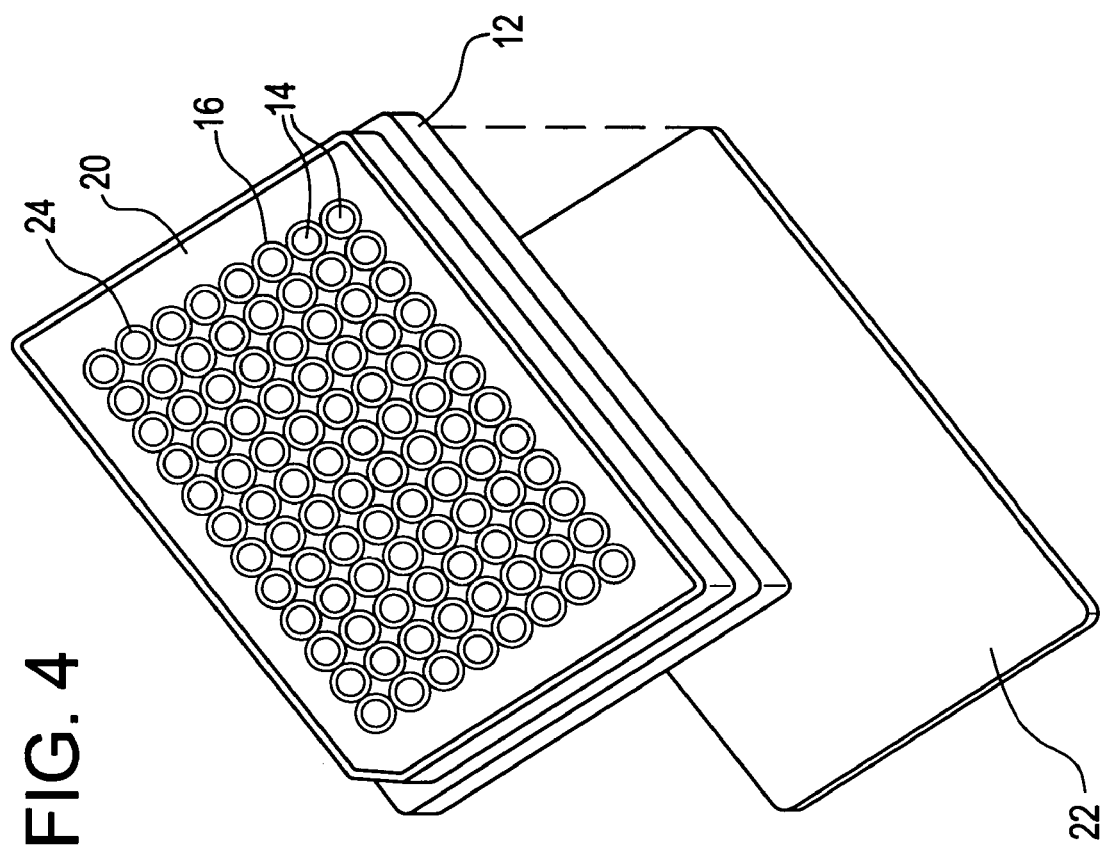
FIG. 4 is an exploded perspective view of the multiwell plate of the present invention.

FIG. 4 is an exploded perspective view of the multiwell plate of the present invention. The upper plate 20 can be seen, containing the peripheral skirt 12, top rim 16, wells 14, and sidewalls 24. The lower plate 22 is preferably flat and sized in order to form well bottoms for all wells of the upper plate 20. Although the lower plate 22 as a whole is substantially flat, it may have relief features formed upon its surface such as ridges, curves, lens, raised sections, diffraction gratings, dimples, concentric circles, depressed regions, etc. Such features may be located on the lower plate such that they shape or otherwise become features of the well bottoms themselves, and may in turn enhance the performance of an assay, enhance or enable detection (as in the case with lenses and gratings), or serve to mechanically facilitate bonding with the upper plate. These relief features may be formed by any number of known methods including vacuum thermoforming, pressing, or chemical etching, laser machining, abrasive machining, embossing, or precision rolling.

Infrared Radiation Cold Welding Process:

The preferred process of manufacture for the plate of the present invention is by employing infrared radiation absorbed at the interface between the upper plate and lower plate that in combination, form a multiwell plate. The upper plate is formed by using standard injection molding techniques on the organic polymeric material used. Infrared absorbing particles are added to the batch mixture. In the case of a carbon black pigmented upper plate, the carbon black itself serves as the infrared absorbent material. If transparent well walls are required, an infrared absorbing transparent pigment must be used (e.g. laser dyes such as IR-792 perchlorate available from Aldrich Chemical). Concentrations for the laser dyes are preferably greater than $5\times10^{-6}$ $g/cm^2$ at the interfacial region between upper and lower plates. The organic polymeric material of choice is molded into an upper plate 20, as shown in FIG. 4, consisting of a peripheral skirt 12, an array of open ended, cylindrical wells 14 defined by sidewalls 24, and having top rims 16.

Figure 6:
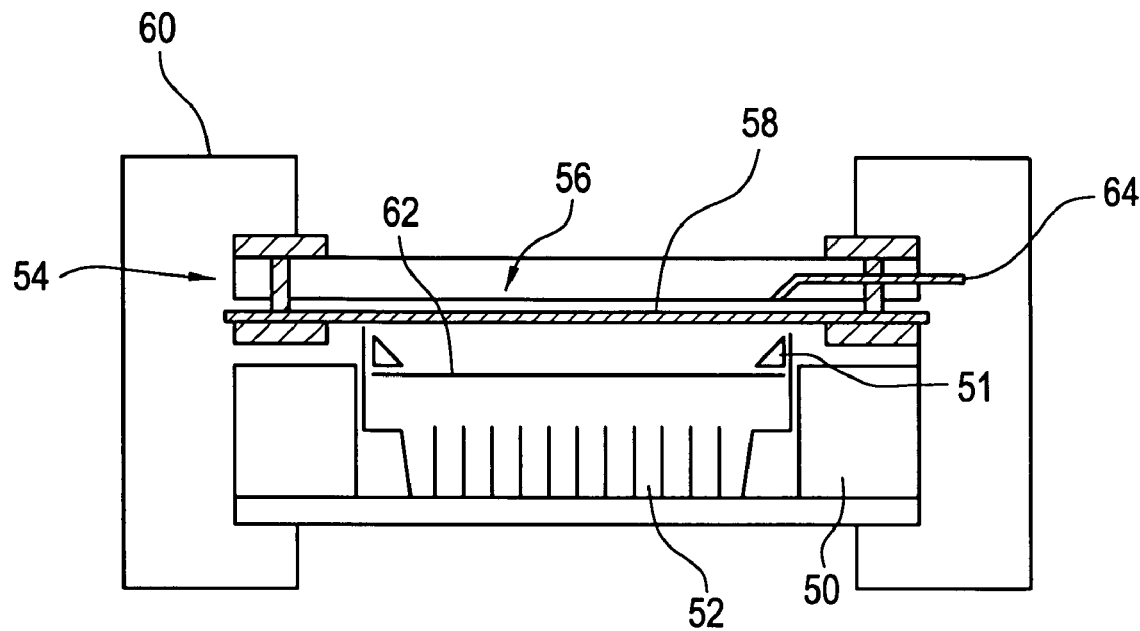
FIG. 6 is a schematic cross sectional view of the manufacturing apparatus used in the present invention prior to introducing gas.
Figure 7:
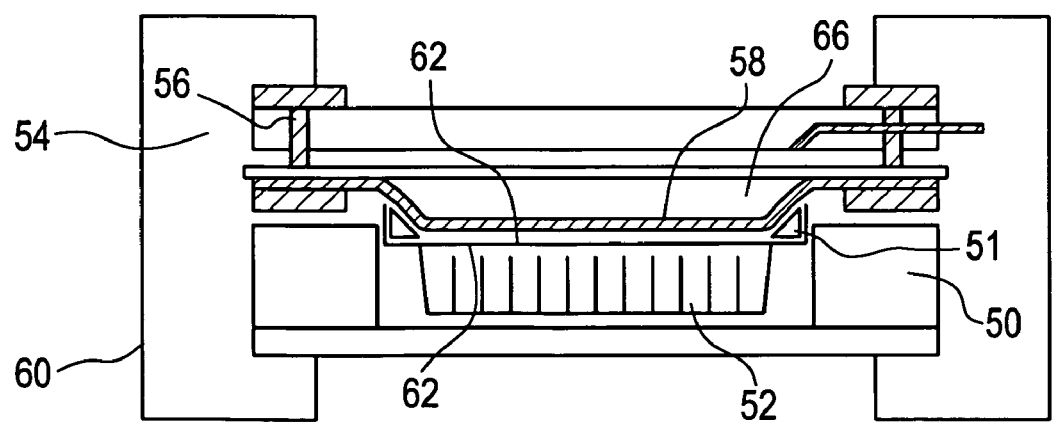
FIG. 7 is a schematic cross sectional view of the manufacturing apparatus used in the present invention after introduction of gas to inflate the bladder formed by the PDMS layer.

Next, a glass sheet is obtained as the lower plate, the length and width dimensions of which conform generally a size capable of covering an entire array of wells from an industry standard multiwell plate. The thickness is variable, but preferably in the range previously discussed. Prior to assembly, the glass is extensively cleaned by pyrolysis, plasma, UV/ozone, or piranah solution. The two plates are firmly held together in contact using an infrared assembly machine manufactured for example by Branson Ultrasonics (Danbury, Conn.). A cross sectional schematic drawing of the assembly is shown in FIGS. 6 and 7. A bottom metal feature 50 aligns and holds the upper plate 52. An upper feature 54 is comprised of an infra red transparent polycarbonate sheet 56 of sufficient thickness to withstand at least 25 psig, bolted to a platinum catalyzed polydimethylsiloxane (PDMS) sheet 58 of sufficient thickness also able to withstand at least 25 psig. An appropriately lower plate 62 is placed on top of the upper plate 52. During the welding process, metal C-clamps 60 hold the upper feature 54 and lower feature 50 together. The clamp 60 is attached to the upper feature and lower feature by appropriate hinges, bolts, and clamping means strong enough to withstand 25 psig and is made stainless steel or aluminum, for example. A metal frame 51 is placed inside the skirt of the upper plate in order to properly align and locate the lower plate over the wells of the upper plate. Once the clamps are securely fastened, an appropriate gas, e.g. nitrogen, is introduced to the space between the polycarbonate sheet 56 and the PDMS sheet 58 by means of a gas inlet 64. As shown in FIG. 7, the PDMS sheet is forced downward by the inflating gas pocket 66. This inflation has the effect of uniformly forcing the two parts (upper plate and lower plate) into intimate contact. The pressure may be adjusted, but the preferred range is 4-25 psi, more preferably, 5-7 psig.

Energy is then supplied by an array of infra red laser diodes transmitting at approximately 820 nm. This energy passes through the polycarbonate sheet, the PDMS sheet, and the glass lower plate and is targeted at the portion of the upper plate that contacts the lower plate. The infra red absorbing molecules forming part of the matrix polymer of the upper plate, absorb this energy, transfer it to the polymer and thereby melt the portion of the upper plate which interfaces the glass of the lower plate. The organic polymeric material of the upper plate must be brought to its melting temperature in order for it to wet the glass and then for the covalent attachments to occur between the silane in the polymer and the hydroxyl groups of the glass at the interface, since the reaction of the covalent attachment is driven by the presence of heat and moisture. Assembly should preferably take place under clean room conditions. In fact, a carbon filter within the unit will effectively remove smoke and residual organics created from the welding process, as well as protect the lasers from out-gassing, and add clean air to the system. Further, it is helpful to sparge the unit with helium while the welding process is initiated and carried out. This helps achieve a clean part and limits any unwanted surface oxidation or other reactions on the exposed surfaces.

The array of infra red diodes is focused to give a uniform line of energy about 2 mm wide on the bottom surface of the upper plate. The clamp 60 described in FIG. 6 is translated at a constant speed to scan the line of energy over the entire surface to be bonded. The scan speed is variable, but preferably in the range of 0.1-1.0 inches/second. Operation power on the instrument is typically in the range between 45 and 75%. The laser can be turned off at the end of the scan to prevent damage to the clamp or translation mechanism. In a preferred embodiment the metal frame 51 is used to define the area to be scanned and to hold the glass lower plate 62 in alignment. This metal frame also takes up the energy until the laser output is stable and to take up the energy of any over scan. If necessary the frame can be cooled. Further, any excess energy passing through the entire assembly of upper and lower plates (e.g. in well areas) can be absorbed into the base of the assembly structure which is preferably fitted with cooling equipment. The combination of the frame and the base of the instrument receive the laser energy not used in welding. Since other materials are IR transparent, the heat buildup in the polycarbonate window 56, the PDMS bladder 58, and the glass 62 is minimal. Heating only occurs over the scan line, so after the scan line has passed over a particular area, the lower and upper plates in that area are bonded, while the area not yet scanned is still held together by the clamping means previously discussed. Because of the clamping, the registration between upper and lower plate during the welding process remains unchanged; this is especially important when exact alignment of features in the lower plate is required.

The covalent grafting is achieved in a two step reaction. First, a hydrolysis reaction occurs in which a water molecule hydrolyzes a silicon-ethoxy bond in the silane, releasing a molecule of ethanol and leaving a silicon hydroxide function bond. Second, a condensation reaction occurs in which two silicon hydroxide functionalities, one from the silane and one from the glass surface, eliminate a water molecule, giving rise to a siloxane bond. The resultant siloxane bonds grafting the upper and lower plate together are extremely stable.

The infrared welding technique is considered a "cold welding" technique because it focuses the heating only in the contact zone interface at the bottom of the sidewalls defining the open bottom of the upper plate. This allows the organic polymeric material forming the remainder of the upper plate to remain rigid and cold, just as the glass material remains so. Further, the use of an infrared laser allows the organic polymeric material to be heated very quickly and only a small amount of heat is added at the interface, which is quickly radiated. This has the effect of preventing the polymeric material of the upper plate from expanding, and therefore remains inflexible. In contrast, conventional methods of heating would cause the entirety of the upper plate to stretch, and eventually become pliable, due to the slow heating and cooling processes inherent in these methods.

Figure 5:
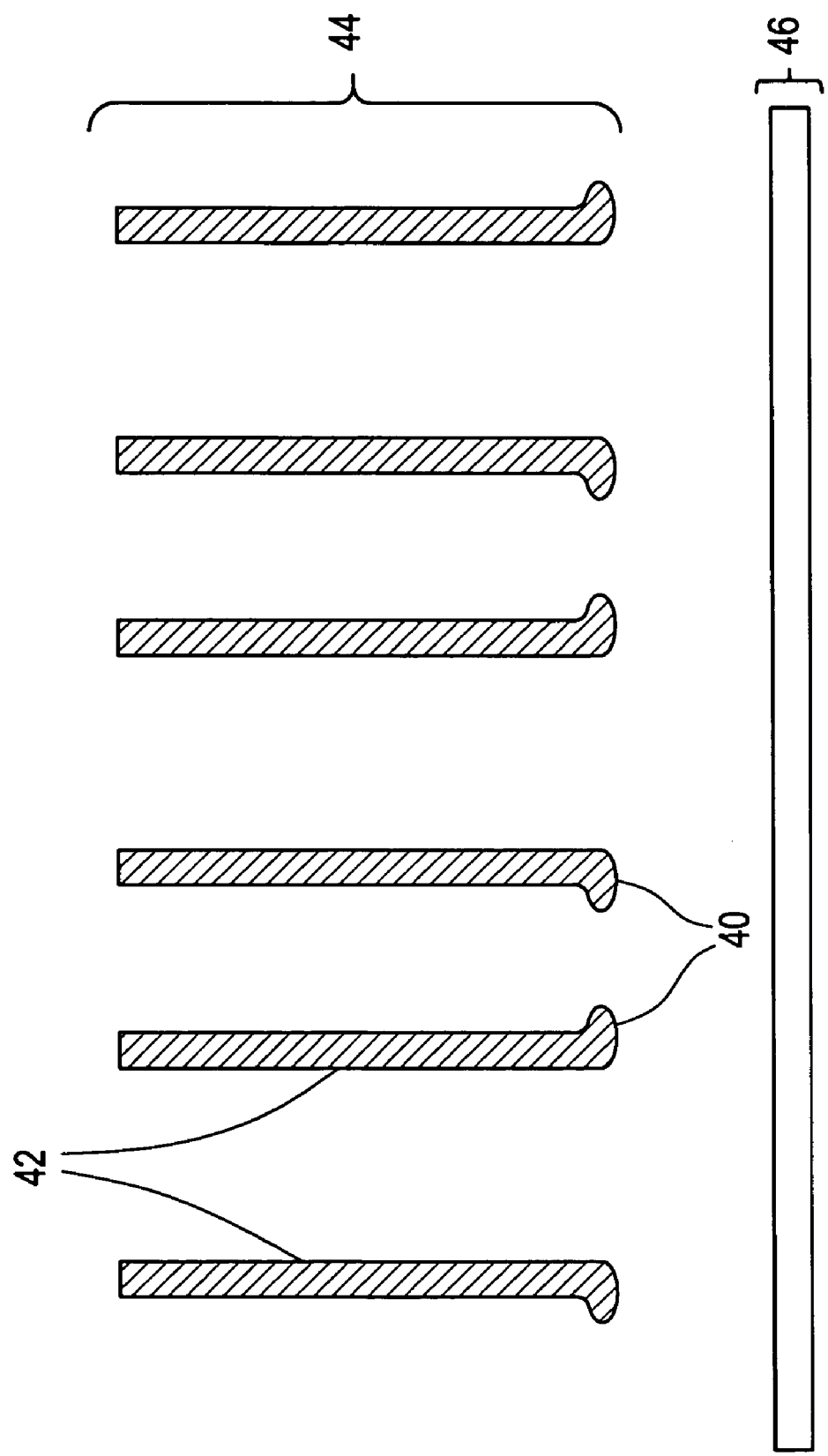
FIG. 5 is a partial exploded cross section view of one embodiment of the multiwell plate embodying the present invention, showing thin ridges around the perimeter of the well bottoms.

FIG. 5 is a partial exploded cross section demonstrating an alternative design of the upper plate which provides more surface area for the interaction between the polymer and the glass lower plate. A beaded rim 40 is molded onto the bottom of the sidewalls 42 of the sample wells making up the upper plate 44. These beads directly contact and covalently bond to the surface of the lower plate 46 thereby drastically increasing the contact area between plates.

In an alternative embodiment, prior to covalently fusing the upper and lower plate together and as shown in FIG. 3, a biologically or chemically active coating 30 may be applied to the surface of the lower plate 22. This way, after the lower and upper plates are fused to form a multiwelled plate, the well bottoms will have imparted thereupon the coating. Coatings can be introduced by any suitable method known in the art including printing, spraying, condensation, radiant energy, ionization techniques or dipping. The coatings may then provide either covalent or non-covalent attachment sites. Such sites, in or on the bottom well surface can be used to attach moities, such as assay components (e.g., one member of a binding pair), chemical reaction components (e.g., solid synthesis components for amino acid or nucleic acid synthesis), and cell culture components (e.g., proteins that facilitate growth or adhesion). Further, the coatings may also be used to enhance the attachment of cells (e.g., polylysine). It can also be conceived that an array of biomolecules (e.g., DNA sequences) can be printed or otherwise synthesized on the surface of the glass lower plate prior to assembly with the upper plate. Once the upper plate is attached, each well bottom may contain a separate such array. The manufacturing method of the present invention is particularly useful for any embodiment involving application of a coating or other moity. Since only a limited region on the polymeric upper plate and away from the area which becomes the well bottoms is actually heated in order to join the upper and lower plates, the coating remains substantially unaltered and undamaged. In this embodiment, it is assumed that no materials are added to the coatings which would absorb at the wavelength of the particular laser diodes being employed.

Further, it may be contemplated that coatings be applied to the outermost surface of the well bottoms. For example, coatings which affect the optical properties of the well (e.g. color filters, IR filters, UV filters, polarizing filters, photon sieves, antireflective surfaces, etc.) may be added based on the specific assay requirements.

Additionally, the lower plate may have a uniform coating on the contacting surface from which bonding areas are ablated by laser. This technique may be required in instances where an extremely thick coating may affect the integrity of the bond formed using the IR assembly instrument. Since the coating is removed from the areas where the lower and upper plates will intersect, nothing will be present to affect the bond strength. Alternatively, the coating may be applied as a design print in which the bonding areas are free of coating. This printing technique may also be employed to create bottom wells, each having a different functionalized surface based on different coatings. This may be accomplished by printing the varied coatings over the contact surface of the lower plate. The coated regions each align with a particular well from the upper plate. Once bonded, a plate having different coatings in the bottoms of each well is achieved.

Figure 8:
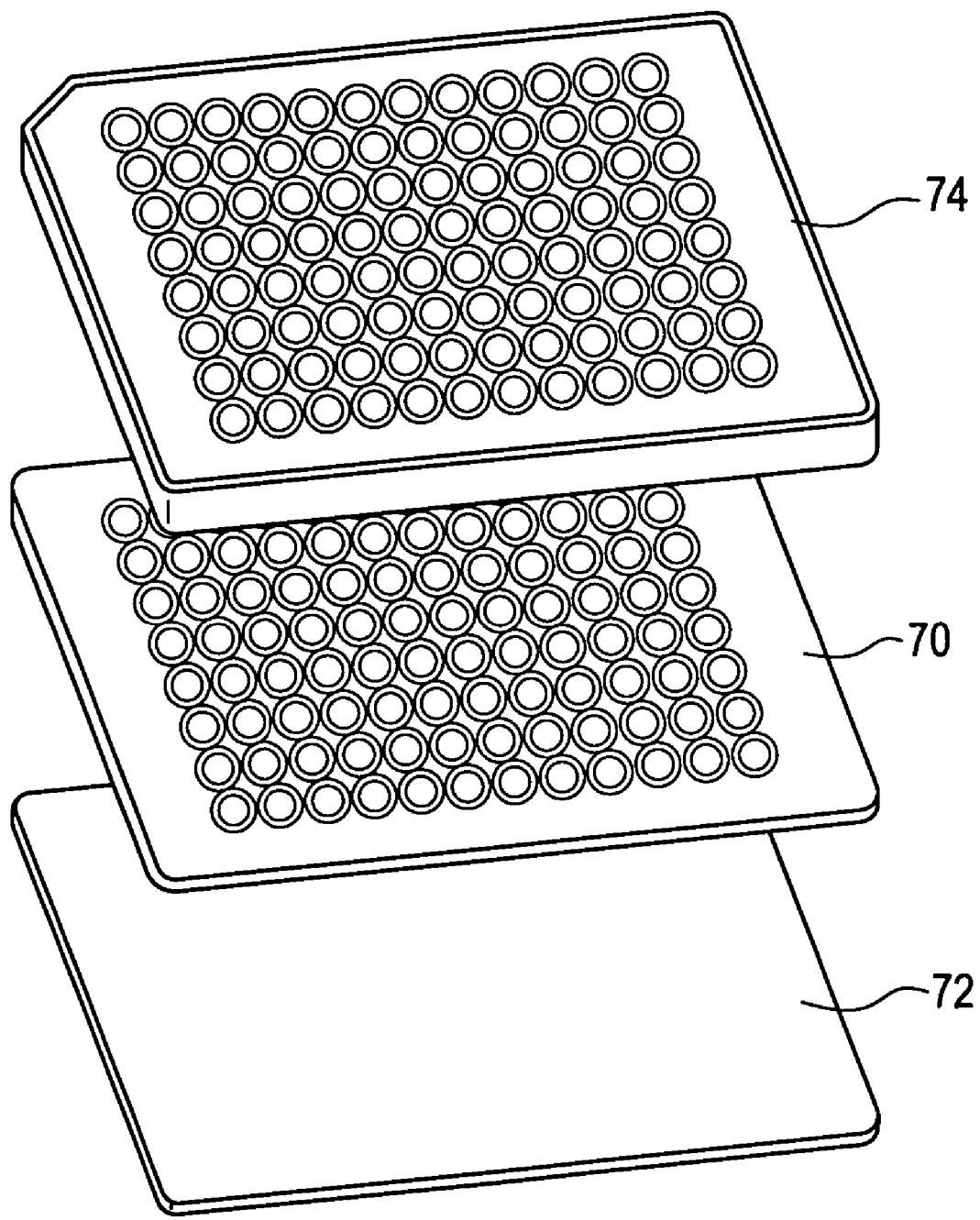
FIG. 8 is an exploded view of an embodiment of the present invention.

Gasket:

In an alternative construction process to that described above and as shown in FIG. 8, instead of having an entire upper plate made of a silane polymer, an interfacial gasket molded from the silane polymer material having IR absorbent characteristics, as previously described, may be employed instead. In such an embodiment, the gasket 70 serves as a bond facilitator for joining the glass bottom 72 with the polymer upper plate 74. This thin film-like gasket, which may also be formed by cutting or by punching a film, preferably has the same footprint dimensions as the finished plate bottom. Although the gasket thickness may vary, it is preferred that it be between 0.5-5 mils in thickness so that the entire gasket may be properly and entirely heated from radiation aimed only at one side. An array of holes or punches are formed therein to align and correspond exactly with the wells of the upper plate. As above, a polymeric material is molded into an upper plate consisting of a peripheral skirt, and array of wells with sidewalls, and top rims. However, it is not necessary that this plate contain a silane material. Preferably, the upper plate is molded from a polymer material which is IR transparent, such as polystyrene, polypropylene, polymethacrylate, polyvinyl chloride, polymethyl pentene, polyethylene, polycarbonate, polysulfone, polystyrene copolymers, cyclic olefin copolymers, polypropylene copolymers, fluoropolymers, polyamides, fully hydrogenated styrenic polymers, polystyrene butadiene copolymers, and polycarbonate PDMS copolymers. Once molded, the upper plate is contacted and aligned with the interfacial gasket, which is subsequently contacted with a lower plate comprising a transparent glass sheet by using the infra red assembly instrument and method previously described. The infra red radiation is then targeted through the glass bottom plate on the interfacial gasket between the upper and lower plate. The radiation passes through the glass and is absorbed by the IR absorbent particles (e.g. carbon black) in the polymer material making up the gasket. This energy absorption heats the gasket only, causing the polymer to reach its melting temperature. This melted gasket material wets the glass where covalent siloxane bonding occurs between the silane in the gasket polymer and the hydroxyl groups of the glass by the same mechanism previously described. The melted gasket material also simultaneously wets and melts the interface between it and the upper plate thereby creating an interpenetrating polymer network bond. In a preferred embodiment, IR radiation is also targeted onto the gasket through an IR transparent upper plate. This way, not only is the interface between glass and gasket heated, but also the interface between upper plate and gasket thereby enhancing bond strength at both interfaces.

As in the previous process embodiment, this method is advantageous in the glass sheet may be treated with a biologically or chemically active coating prior to assembly. Since the heating only occurs in the polymeric material of the gasket and not on the glass itself, the coating or attached biological/chemical moiety remains largely unaffected by the manufacturing process.

It is important to also note that the gasket material serves as an impermeable barrier to fluid transfer between wells and as a barrier to any optical cross-talk.

Silane Coating:

Yet another embodiment for manufacturing the glass bottomed plates of the present invention is to apply a silane coating to the portion of the upper plate which will interact with the glass bottom plate during assembly. In this embodiment, a solvent containing both the silane functionality such as an epoxy silane (e.g., 2-7-oxabicyclo[4.1.0]hept-3-yl-ethyl]silane; Aldrich Chemical) as well as the IR absorbent pigments or dyes in acetone for example, is applied to the bottom portion of a polymer (e.g. a styrenic polymer) upper plate by means of spraying, printing, dipping, brush coating, thermoset, or other means. Although not necessary for practicing the invention, it is believed that the epoxy silane material intercalates in and cross links into the polymer material of the upper plate while the silane functionality remains actively extended. Again, as in previous embodiments, the coated upper plate is contacted with the glass bottom plate, by using the infra red assembly instrument and method previously described. The infra red radiation is then targeted through the glass bottom plate on the silane coating at the interface between the upper and lower plate. The radiation passes through the glass and is absorbed by the IR absorbent particles (e.g. carbon black) in the silane coating. This energy absorption heats the coating only, driving the covalent bond reaction between the silane and the glass where covalent siloxane bonding occurs between the silane and the hydroxyl groups of the glass by the same mechanism previously described. Although IR heating is preferred to help drive the reaction and although not preferred, this type of assembly may be performed without the aid of IR radiation (and therefore without need of IR absorbent particles) simply by applying consistent pressure for an extended period without heating.

As in the previous process embodiment, this method is advantageous in the glass sheet may be treated with a biologically or chemically active coating prior to assembly. Since the heating only occurs in the IR absorbent material at the interface and not on the glass itself, the coating or attached biological/chemical moiety remains largely unaffected by the manufacturing process.

Magnetic Particles:

In an alternative construction process to that described above, instead of infrared absorbing particles, magnetic particles or ferromagnetic particles are mixed into a silane polymer blend in molding a gasket./the magnetic particles are preferably coated with a plasma polymerized coat to prevent the ferromagnetic material from interacting with the well contents. As above, an array of holes or punches are formed therein to align and correspond exactly with the wells of the upper plate. Similarly, a polymeric material is molded into an upper plate consisting of a peripheral skirt, and array of wells with sidewalls, and top rims. Once molded, the upper plate is contacted and aligned with the interfacial gasket, which is subsequently contacted with a lower plate comprising a transparent glass sheet, the length and width dimensions of which are sized generally to cover all wells of the industry standard for multiwell plates. Electromagnetic radiation is then targeted on the interfacial gasket between the upper and lower plate. The radiation passes through the glass and is absorbed by the magnetic particles in the polymer material making up the gasket. This energy absorption leads to vibration of the magnetic particles which in turn heats the gasket only, causing the polymer to reach its melting temperature. This melted gasket material wets the glass where covalent siloxane bonding occurs between the silane in the gasket polymer and the hydroxyl groups of the glass by the same mechanism previously described. The melted gasket material also simultaneously wets and melts the interface between it and the upper plate thereby creating an interpenetrating polymer network bond. As above, in a preferred embodiment, the electromagnetic energy is also directed through the upper plate onto the gasket in order to create a stronger bond between upper plate and gasket.

As in the previous process embodiment, this method is advantageous in the glass sheet may be treated with a biologically or chemically active coating prior to assembly. Since the heating only occurs in the polymeric material of the gasket and not on the glass itself, the coating or attached biological/chemical moiety remains largely unaffected by the manufacturing process.

It may also be conceived that instead of a gasket, a transfer film of ink containing magnetic particles is imparted on the bottommost plane of the upper plate by hot-stamping, dipping, or other known means. When this region interfaces with the lower plate, e.g. glass sheet, it is the target of the prescribed radiation.

Heating of the Lower Plate:

Another alternative method of production is by heating the lower plate such that its temperature is raised to the melting temperature of the polymeric material making up the upper plate. Once contacted with the heated lower plate, the temperature of the upper plate is elevated to it melting temperature. Again, as in the embodiments previously described, the heating of the upper plate only occurs at the interface with the lower plate. However, unlike the other embodiments, the glass plate itself is heated, making this embodiment less attractive for instances in which a coating or biological/chemical moiety is attached prior to assembly. Again, the covalent siloxane bond attachment mechanism is the same as previously described. The process should be run in inert gas conditions to prevent rapid oxidation.

Further, although not necessarily preferred for best quality, it should be noted that the glass bottomed plate of the present invention can be also made using standard insert molding techniques where the glass lower plate is inserted into a mold and the silane functional polymer upper plate is molded onto its surface. The attachment between plates is still largely covalent due to the pendent silane groups in the polymer material of the upper plate and the hydroxyl groups on the glass surface.

Polymer-Polymer Plate Manufacture

It should also be noted that although the above embodiments of the present invention envision the use of a glass lower plate, the process of manufacture is equally effective for attaching a lower plate comprised of a polymeric material or even a polymer sheet. In that case, the attachment is not covalent as described, but relies on a fusion bond. In such an embodiment, a polymer film is used in place of the glass bottom plate. The film is substantially transparent to infra red radiation. Examples of IR transparent material that can serve as the lower plate portion include: polystyrene, polypropylene, polymethacrylate, polyvinyl chloride, polymethyl pentene, polyethylene, polycarbonate, polysulfone, polyolefins, cyclic olefin copolymers, polystyrene copolymers, polypropylene copolymers, fluoropolymers, polyesters, polyamides, polystyrene butadiene copolymers, fully hydrogenated styrenic polymers, and polycarbonate PDMS copolymers. The choice of material will depend on the particular type of assay the multiwell plate is meant to facilitate. In this embodiment, the lower plate may take the form of a plate, film (porous or non-porous), filter, pigment containing films, and cavity containing films. In the case of films, the thickness can vary depending on material and assay requirements, but the present method accommodates plate manufacture with films as low as 1 mil in thickness. Multiwell plates made with films having thicknesses below 5 mils are difficult if not impossible to make using standard injection molding techniques. The extremely thin films that may be employed as bottom wells may allow gas exchange through the well bottom which in turn facilitates call growth and biological activity. As in the glass lower plate embodiment previously described, the polymer lower plate may contain relief features formed upon its surface such as ridges, curves, lens, raised sections, diffraction gratings, dimples, concentric circles, depressed regions, etc. Such features may be located on the lower plate such that they shape or otherwise become features of the well bottoms themselves, and may in turn enhance the performance of an assay, enhance or enable detection (as in the case with lenses and gratings), or serve to mechanically facilitate bonding with the upper plate.

An upper plate is either molded from material having IR absorbent properties (e.g. carbon black), or has IR absorbent characteristics at the interface at which the upper and lower plates are to be bonded. For example, an IR transparent upper plate may be employed onto the bottom of which an IR absorbent material has been hot stamped, painted, thermoset, sprayed or otherwise imparted. Examples of suitable IR absorbent materials include: carbon black pigment, laser dye molecules, or other IR absorbent materials commonly known to those of skill in the art. It is also conceivable that the bottom plate have a patterned area of IR absorbent material imparted onto its bonding surface which would properly align with a wholly IR transparent upper plate.

Prior to assembly, the polymer lower plate, whether film or rigid plate, should be cleaned with an ionized air stream in order to remove any particulates as well as relieve static buildup. The polymer may also be plasma treated to drive off any unwanted moisture and to activate the surface with reactive functional groups. This activation may in turn enhance the polymer-polymer interaction between upper and lower plates as well as create a biologically reactive surface. In fact, bonding certain unlike polymers by the disclosed method may require plasma treatment of the interactive surfaces.

Plasma treatment may be accomplished by using a plasma chamber (Branson 7150, Branson Ultrasonics, Danbury Conn.). The RF frequency is preferably set at 13.56 MHz, the pressure is 180 millitorr, using oxygen, and the time of treatment is approximately 1.0 minute.

Again, as in previous embodiments, the upper plate is contacted with the bottom plate, by using the infra red assembly instrument and method previously described. The infra red radiation is then targeted through the IR transparent bottom plate on the IR absorbent material at the interface between the upper and lower plate. Heating occurs only in areas that have been predetermined to absorb IR radiation. The heating combined with pressure applied to enhance the welding process, allows for fusion along the interface between parts. Unlike in an injection molding operation where conditions such as extreme heat will polarize and stretch the polymer making up the well bottom, this selective heating method assures that only the interface is heated, thereby preventing deformation of the well and preserving the optical qualities of the lower plate/film.

When using a non self-supporting thin film as a bottom plate, it is preferred that a sheet of glass be used in the IR assembly instrument as backing for the film in order to help create the necessary pressure for bonding to the upper plate. FIGS. 9-10 are schematic cross-sectional representations of the clamping mechanics within the IR assembly instrument. FIG. 9 is an exploded view of the parts and the clamping mechanism employed in this embodiment. An upper plate 80 taking the form of an open welled polystyrene multiwell plate is fixed in place within the instrument. The lower plate 82 taking the form of a polystyrene film is located on top of the upper plate 80. A sheet of glass 84 sized to substantially cover the lower plate/film is located on top of the lower plate 82. A polycarbonate layer 86 is held within an aluminum frame 88. A PDMS bladder 90 is clamped to the aluminum frame 88. In FIG. 10, all pieces are in intimate contact, gas has been pumped into the area between the polycarbonate 86 and the bladder 90 thereby creating uniform pressure on the glass sheet 84. The pressure applied to the glass by the bladder may be between 4-25 PSI, but is preferably between 5-7 PSI. As previously described, IR radiation is targeted through the polycarbonate 86, the PDMS bladder 90, the glass 84, and the polystyrene film 82 onto the contact surface of the polystyrene upper plate 80. The IR radiation travels directly through the upper plate in the open welled sections, without heating. The upper and lower plates are thermally bonded together and the part is removed from the instrument. The glass sheet does not bond to the lower plate and therefore is easily removed. It is also important to note that throughout this process, nothing contacts the portion of the film that is to become the bottom of the wells. This is important because it preserves the optical integrity and biological integrity of the well bottom.

The method as described, when used with films which are non-self supporting, creates well flatness not before seen in plates having upper and lower plates joined together by non-adhesive means such as insert molding, sonic welding, and heat welding. Non-self supporting films are those which are unable to support themselves in a horizontal plane when clamped on one end. This may be tested by clamping a 6 cm×1 cm sample on one end and held outwardly in a horizontal position. If the sample is not sufficiently rigid to maintain the plane, it shall be considered, for purposes of this disclosure, non-self supporting.

As with previous embodiments, the film or polymer plate (lower plate) may be treated with a biologically or chemically active coating prior to assembly. Since the heating occurs only at the interface between polymer parts, the IR transparent coated portion making up the well bottom will remain unaffected. Further, a unique characteristic of this assembly process allows for only the well bottoms to be coated or functionalized, and not the well walls. This can have important advantages in many assay systems where biomolecular attachment to the well walls can cause problems with assay results. For example, in cell based assays, it is important that cells adhere to the transparent bottom of the well in a monolayer. When cells attach to the side walls of the well, they often will later retract and settle onto the well bottom, killing the cells of interest attached there. In a plate having wells with non-functionalized side walls and functionalized bottoms, one can be sure that the desired assay activity occurs on the well bottoms. It should be noted that this advantage is equally applicable to the glass bottomed plate embodiment.

Experiment 1

Figure 11:
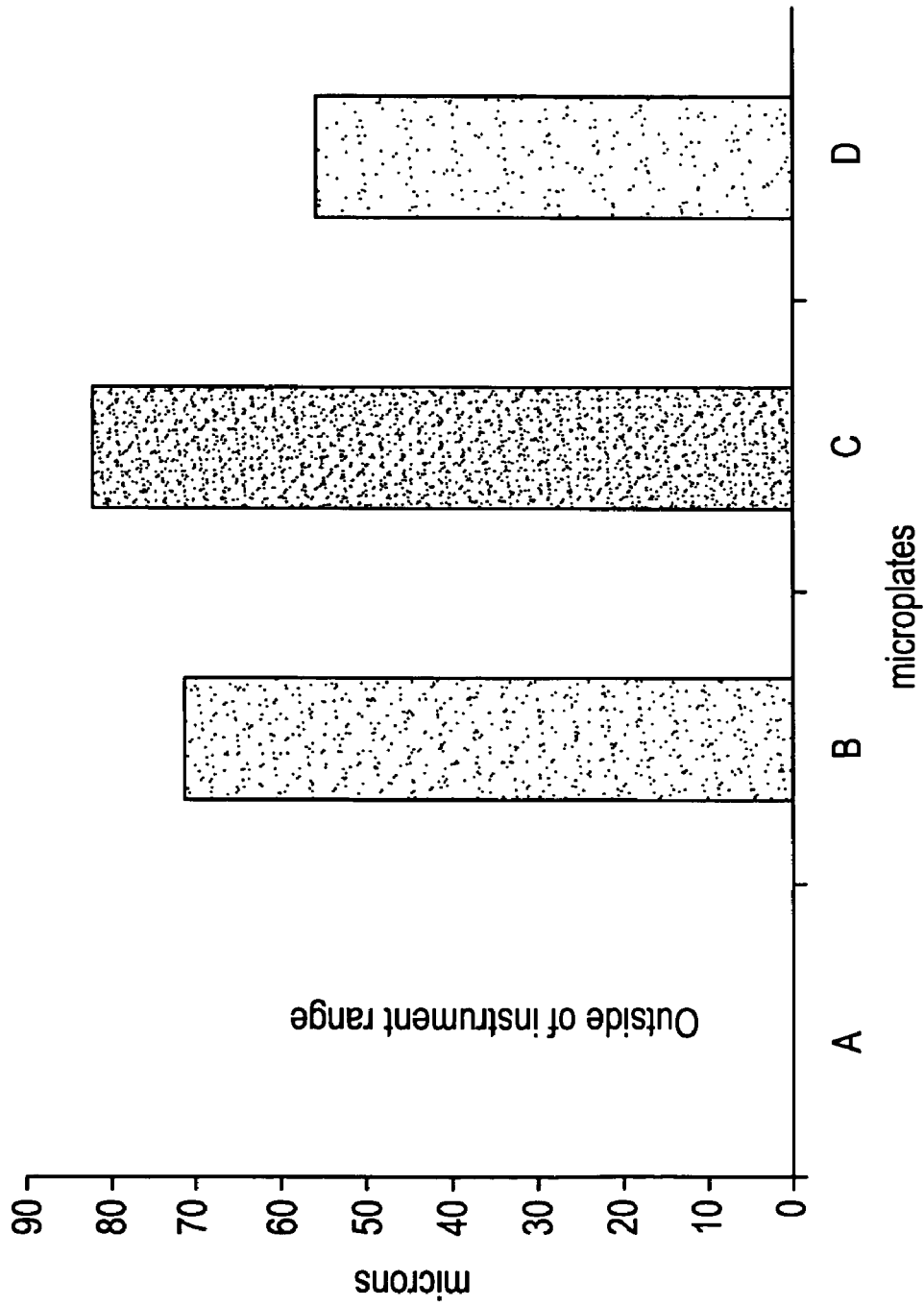
FIG. 11 is a bar graph representation comparing across plate flatness of 96 well plates made with the present process and similar plates made with a standard molding process.

In order to demonstrate unique flatness characteristics both across individual wells as well as across the entire bottom of a multiwell plate, measurements were taken from plates made by the present method as well as plates made from standard injection molding/insert molding techniques. FIG. 11 demonstrates the flatness of several plates as measured by a Tencor (model P20) profilometer. Measurements were taken across the bottom portion of several types of multiwell plates. Each plate was measured across several different lines and results were averaged. First, several Greiner μClear™ 96 well black/clear plates, made from an insert molding technique, whereby a 5 mil thick optically clear polystyrene film is placed in a mold and an upper plate is molded against it, were measured. As shown in FIG. 11, column A, the bottoms of these plates were not even flat enough across their length to be recorded by the instrument. Next, several Corning Costar™ 96 well black/clear plates, also made from an insert molding technique whereby a 25 mil thick separately molded optically clear polystyrene lower plate is placed in a mold and a black polystyrene upper plate is molded against it, were measured. The black polystyrene plate was achieved by standard practice of adding carbon black to the batch mixture in concentration of 1 part carbon black material (Furnace Black-Black Pearl 430, Clarion Corp.) to 50 parts virgin polystyrene (685D, Dow Chemical Corp.), and injection molding the plate. As shown in FIG. 11, column B, the average flatness across the plates was in the range of 70 microns. Next, several Corning Costar™ 96 well black/clear plates made from an insert molding technique whereby a 5 mil thick optically clear polystyrene film is placed in a mold and a black polystyrene upper plate is molded against it, were measured. As shown in FIG. 11, column C, the average flatness across these plates were in the range of 80 microns. Finally, several plates made by the present method from a 5 mil optically clear polystyrene film IR radiation bonded to a black polystyrene upper plate were measured. As shown in FIG. 11, column D, the average flatness across these plates is approximately 55 microns.

Experiment 2

Figure 12:
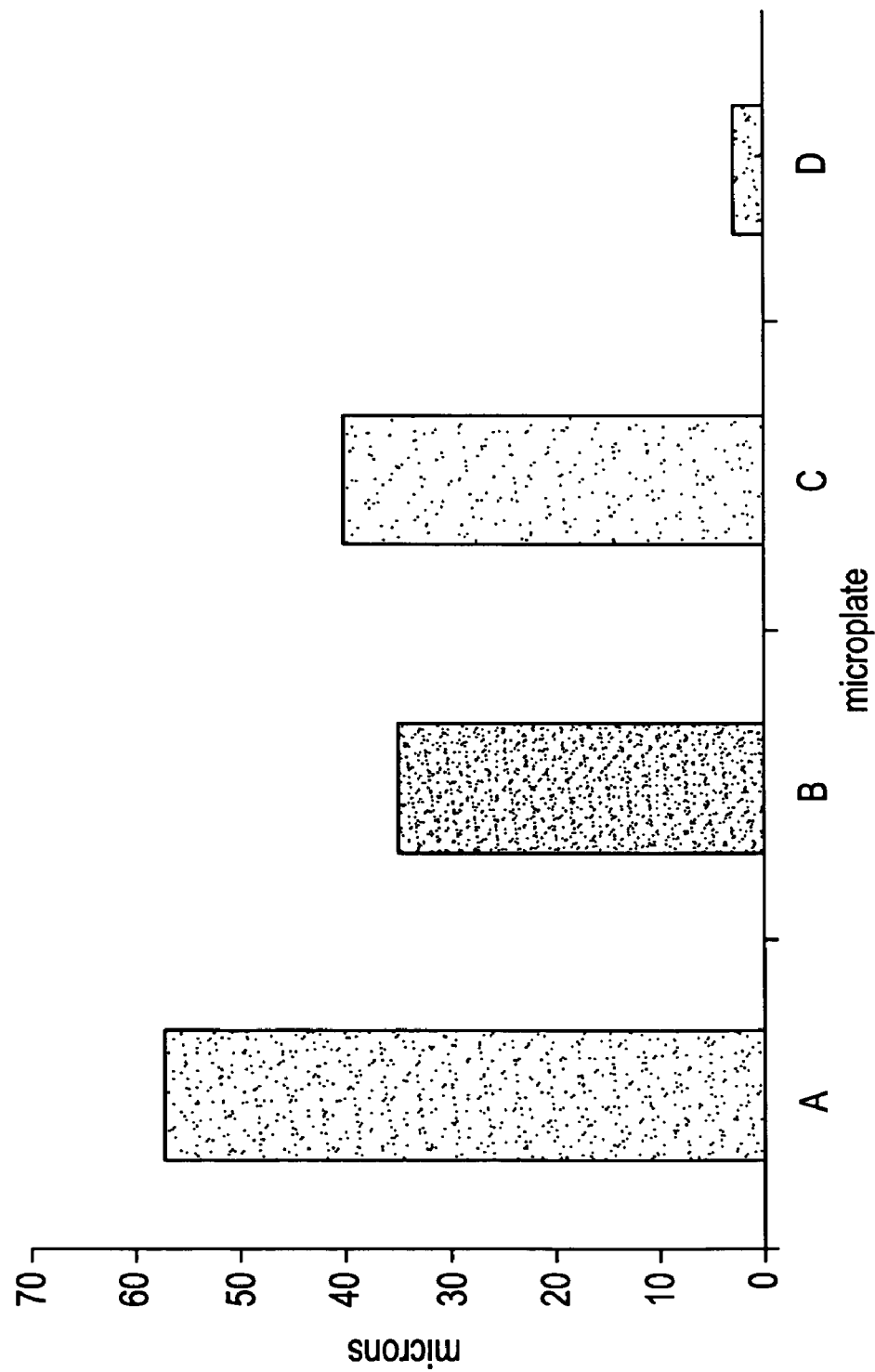
FIG. 12 is a bar graph representation comparing across well flatness of 96 well plates made with the present process and similar plates made with a standard molding process.

Similarly, the plates of example 1 were measured across the bottoms of multiple randomly selected individual wells for flatness. FIG. 12 shows the results of the experiment. The Greiner μClear™ plate, column A, has well bottoms with an average flatness approaching 60 microns. The Corning Costar 25 mil bottom plates, column B, have an average well flatness of approximately 35 microns. The Corning Costar 5 mil bottom plates, column C, have an average well flatness of about 40 microns. The 5 mil bottom plates made from the present method have an average well flatness of less than 5 microns.

Experiment 3

Figure 13:
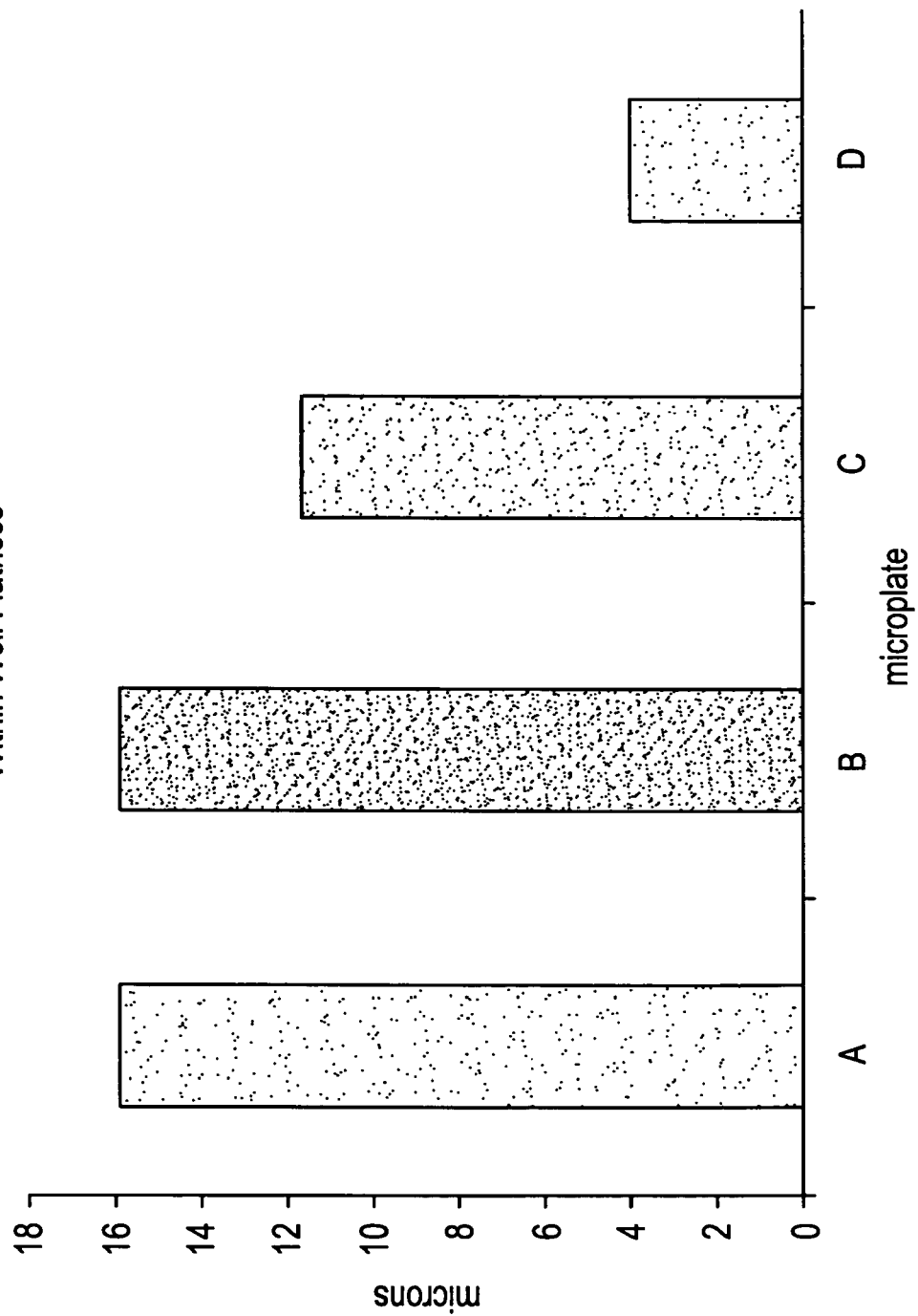
FIG. 13 is a bar graph representation comparing across well flatness of 384 well plates made with the present process and similar plates made with a standard molding process.

Across well flatness was also measured for plates manufactured in the same manner, with the same materials as in Example 1, but of a 384 well format instead of 96. Again, the flatness measurements for the plate made by the instant invention are superior in flatness to plates made by standard insert molding techniques for flatness across an individual well. FIG. 13 shows the results of the experiment. The Greiner μClear™ 384 well plate, column A, have well bottoms approaching an average flatness of 16 microns. The Corning Costar™ 25 mil bottom plates, column B, also have an average well flatness of approximately 16 microns. The Corning Costar™ 5 mil bottom plates, column C, have an average well flatness of about 12 microns. The 5 mil bottom 384 well plates made from the present method have an average well flatness of less than 5 microns.

Experiment 4

Several 1 by 3 inch glass microscope slides were employed to determine the relative strength of the silane/glass bond interaction that plays a significant part in some embodiments of the present invention. Two types of interactions were studied. First, a 20 mil thick non-silane containing polymer material was attached to a glass slide using the IR assembly instrument and process as previously described. Next, a 20 mil thick silane containing polymeric material was attached to a glass slide using the IR assembly instrument and process as previously described. The polymeric material in each instance was sized to overlap approximately an inch beyond the glass. Once assembled, each part was stabilized with a clamp, and the overlapping polymer portion was clamped and pulled with a force at a right angle to the plane established by the glass slide. The total pounds of force required to separate the glass from the polymer on each slide was recorded.

The non-silane polymeric material registered a result of 0 pounds of force required for separation. The silane containing material could not be separated from the glass upon exacting the maximum amount of force (40 lbs.) from the measuring instrument. This experiment demonstrates the effectiveness of the bonding interaction facilitated by the siloxane linkages.

Experiment 5

Several 96 well plates were constructed using the assembly method of the present invention. The plates were constructed of a high density polyethylene upper plate, and a 1 mm thick glass bottom bonded together with a vinyl silane gasket. The plates were then subjected to a pressure test to discern the force required to separate the parts. An Ametec™ pressure gauge was used wherein the gauge unit was inserted into various wells and pressed against the well bottoms. No separation or distortion of the plate occurred through 20 pounds of pressure, the outer limit of the instrument. This test demonstrates the effectiveness of the bond created by employing a gasket device as described herein.

Experiment 6

Figure 14:
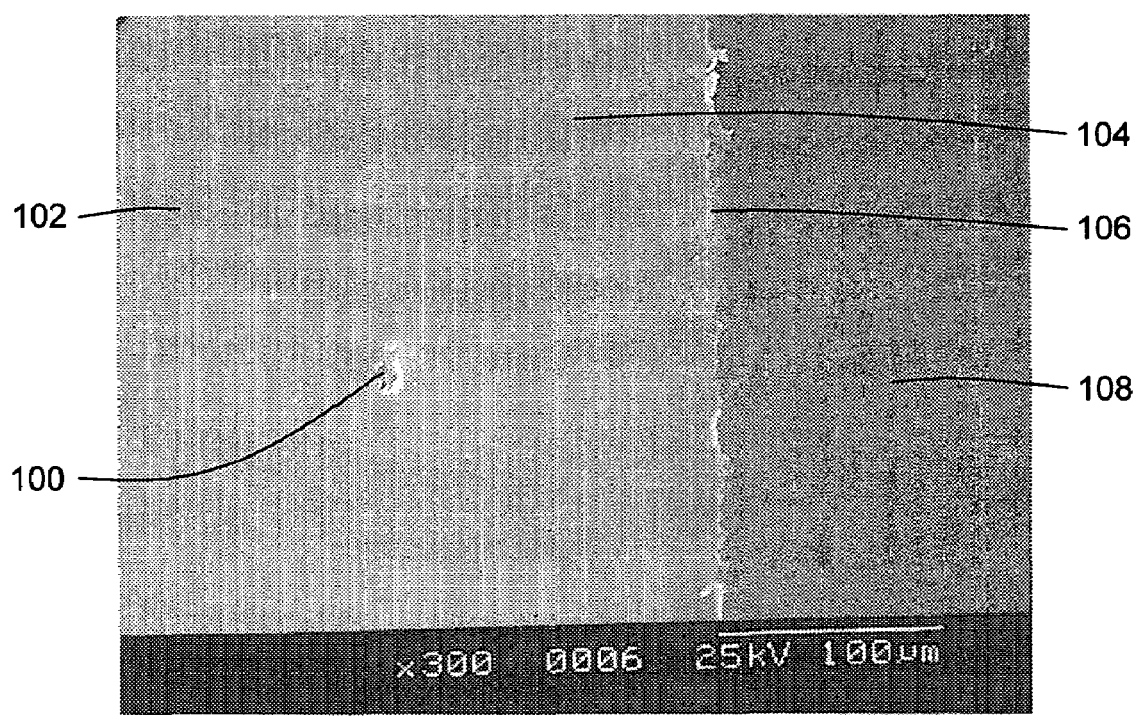
FIG. 14 is a 300× scanning electron micrograph of a cross section of the bonding zone between a polystyrene upper plate and a polystyrene lower plate assembled according to the present invention.

A black polystyrene 96-well upper plate was bonded to a 5 mil thick optically clear polystyrene film lower plate using the infra red assembly process herein described. The plate was then cut in cross section in order to exposed the bonding zone. FIG. 14 is an SEM micrograph of the cross-sectional cut at a resolution that does not differentiate the black upper portion from the optically clear lower portion. A knit line 100 marks the boundary between upper plate 102 and lower plate 104. The bottom 106 of the multiwell plate is marked by the transition to air 108. This micrograph displays that the polystyrene parts weld together so well that the intersection between upper and lower plate cannot be determined but for the knit line 100.

Experiment 7

In order to demonstrate the effects of the welding process of the present invention on a pretreated surface, an experiment was performed studying biological compatibility of plates manufacture according to the present method. Three groups of 96 well plates were assembled according to the present process, combining a 96-well black polystyrene upper plate with an optically clear 5 mil thick polystyrene film lower plate. Prior to assembly, the lower plates were treated in different ways. In a first set of plates, the lower plates were untreated; in a second set of plates, the lower plate surface, which was to become the well bottoms, was treated with plasma radiation as described above; and in the third group of plates the lower plates were treated with plasma radiation and coated with collagen. After assembly, all fully assembled 96-well plates were tested for biological compatibility by attempting to grow cells on the well surfaces.

Figure 15:
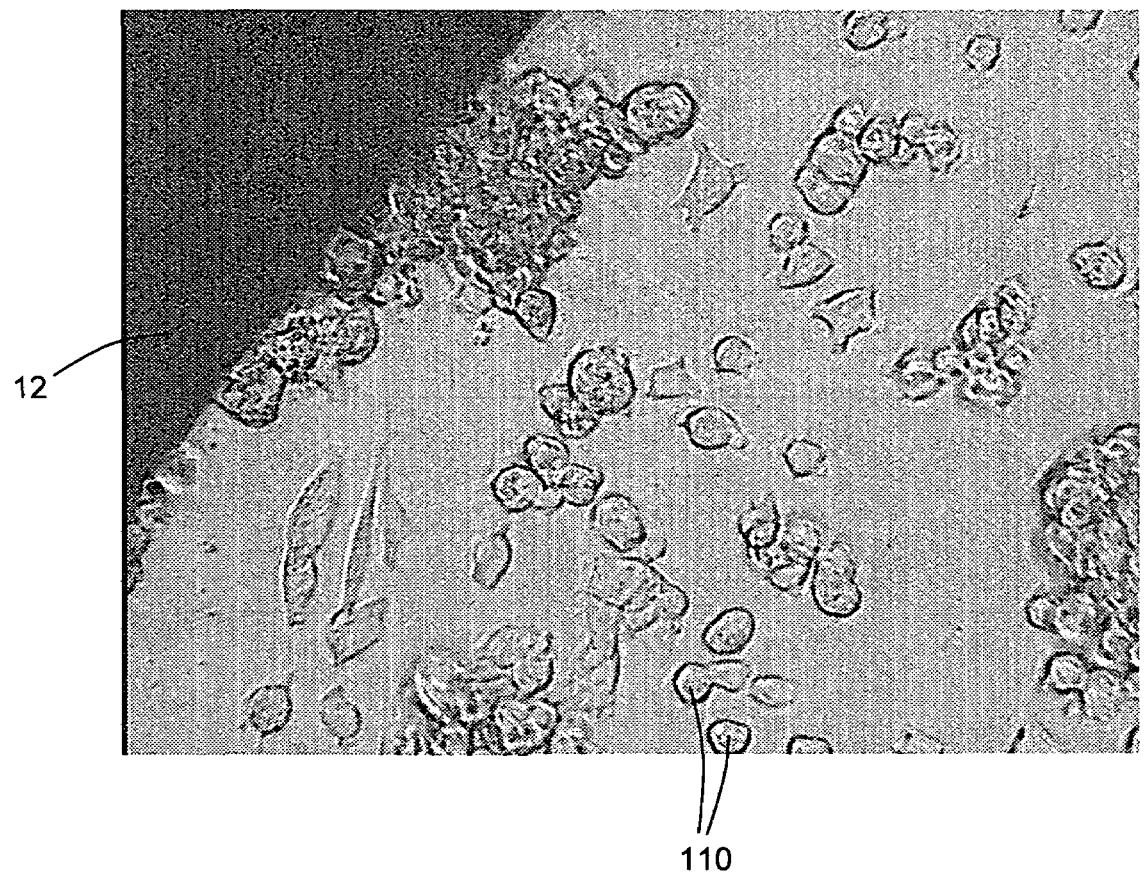
FIG. 15 is a 200× magnification photograph of cells within a well of a 96 well plate created by the assembly process of the present invention. The surface is untreated.

In the first group of plates, as shown in the photograph of FIG. 15, the untreated surface was not compatible with achieving a monolayer of cell growth. Cells 110 are widely distributed and non-confluent. Some cells are bunched around the edge of the well 112, while other areas around the well edge are completely free of cell attachment.

Figure 16:
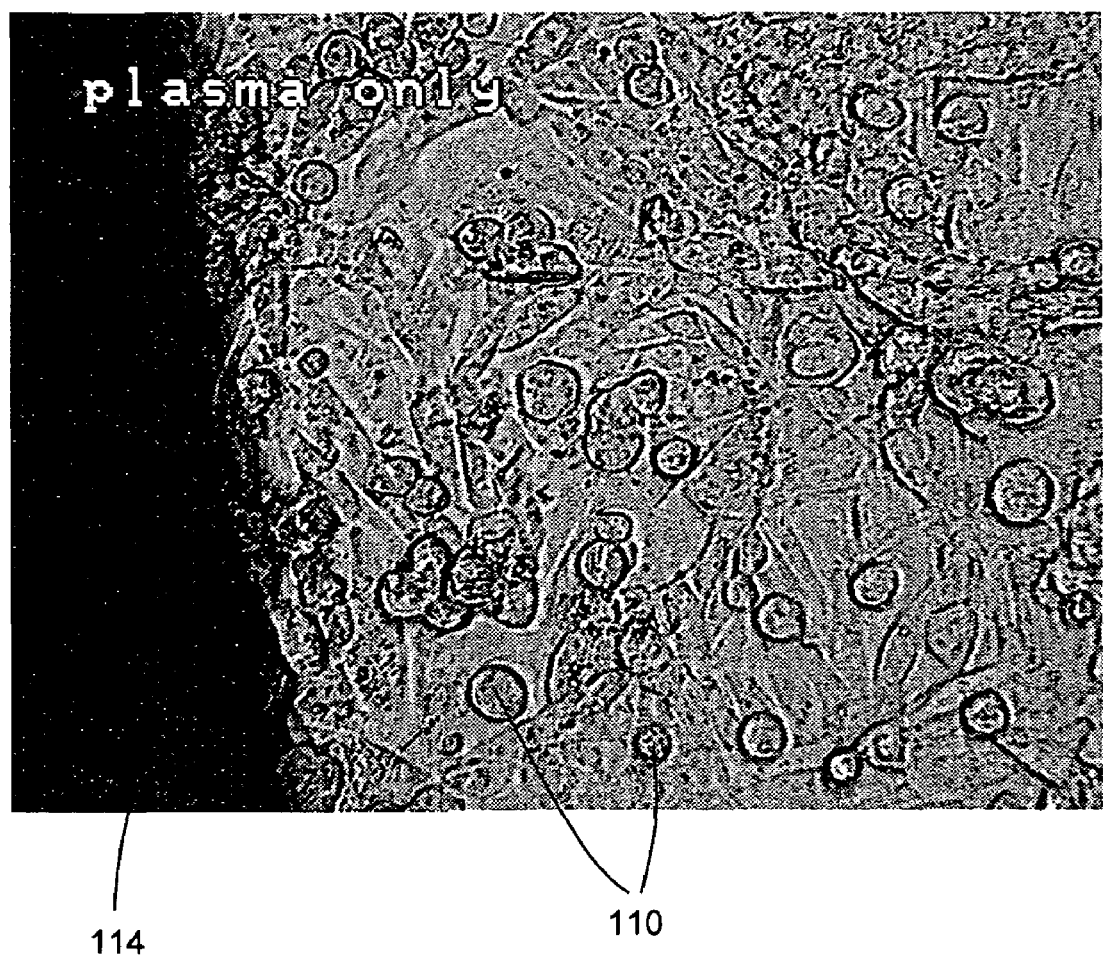
FIG. 16 is a 200× magnification photograph of cells within a well of a 96 well plate created by the assembly process of the present invention. The surface is treated with plasma.
Figure 17:
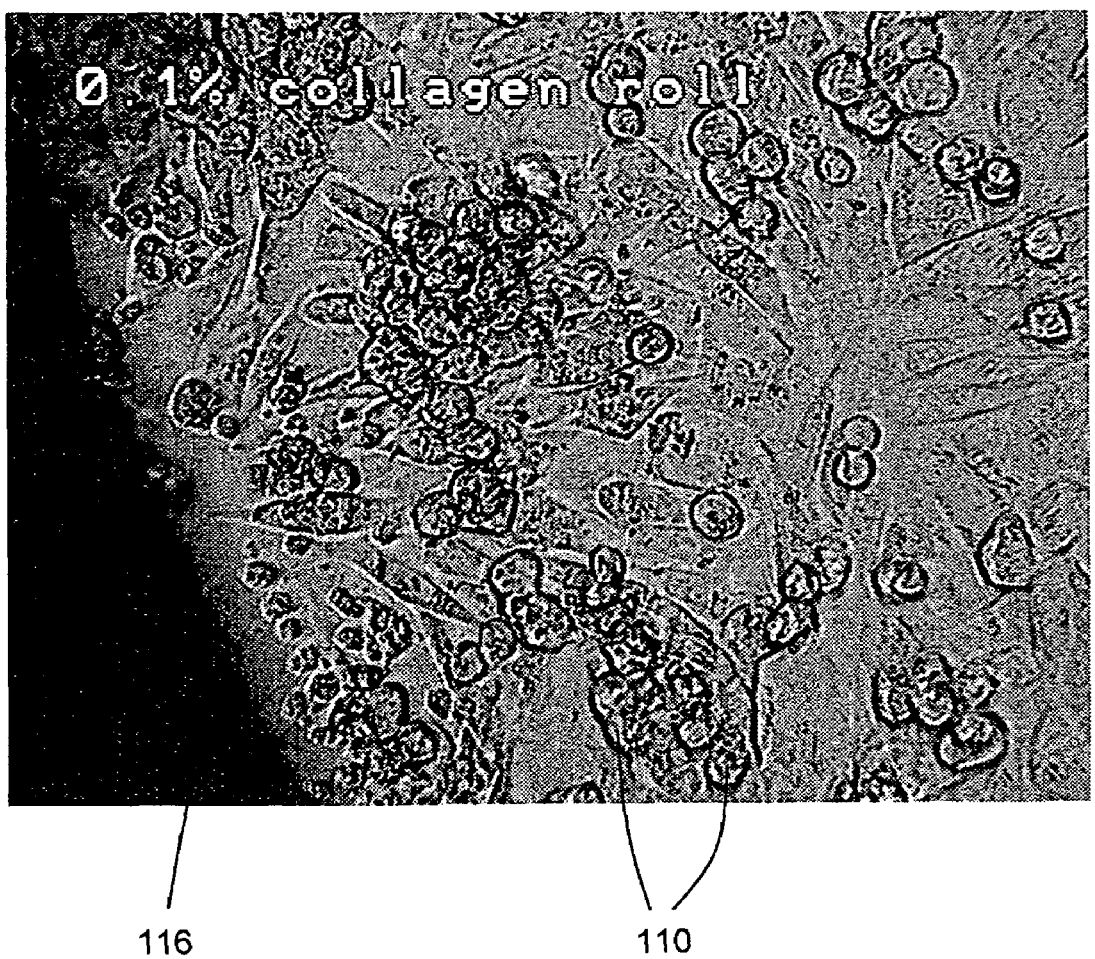
FIG. 17 is a 200× magnification photograph of cells within a well of a 96 well plate created by the assembly process of the present invention. The surface is treated with plasma and collogen.

In the second and third group of plates, as shown by representative photographs FIGS. 16-17, respectively, cell growth is robust and cells 110 are evenly distributed across the well bottom surface. Cells have flattened out indicating good adhesion to the surface. Further, and importantly the cell attachment and growth occurs right up to the edge of the wells 114, 116. This demonstrates that the cold welding assembly process does not adversely affect these pretreated surfaces.

Although the invention has been described in detail for the purpose of illustration, it is understood that such detail is solely for that purpose and variations can be made therein by those skilled in the art without departing from the spirit and scope of the invention which is defined by the following claims.

We claim:

1. A method of making a multiwell plate comprising the steps of:
providing an upper plate having an array of open ended wells, said upper plate being formed from an organic polymeric material having a predetermined melting temperature and comprising a silane functional polymer;
providing a substantially flat transparent lower plate, said lower plate being comprised of an inorganic material;
contacting said upper plate to said lower plate at an interface;
heating said upper plate at said interface to the melting temperature of said polymeric material; and whereby said upper plate and said lower plate are bonded together.

2. The method of claim 1 wherein said upper plate and said lower plate are covalently bound.

3. The method of claim 1 wherein said upper plate further contains infra red absorbent particles blended therethrough, and said upper plate is heated at the interface by infra red radiation directed through the lower plate.

4. The method of claim 1 wherein the silane functional polymer is poly (ethylene-co-trialkoxyvinylsilane).

5. The method of claim 1 wherein the inorganic material is glass.

6. The method of claim 5 wherein the glass is a borosilicate glass.

7. A method of making a multiwell plate comprising the steps of:

providing an upper plate having an array of open ended wells, said upper plate being formed from an organic polymeric material comprising a silane functional polymer having a predetermined melting temperature;

providing a substantially flat transparent lower plate, said lower plate comprising of an inorganic material;

heating said lower plate to the melting temperature of said polymeric material;

contacting said upper plate to said lower plate at an interface whereby said upper plate and said lower plate are bonded together.

8. The method of claim 7 wherein the silane functional polymer is poly (ethylene-co-trialkoxyvinylsilane).

9. The method of claim 7 wherein the inorganic material is glass.

10. The method of claim 9 wherein the glass is a borosilicate glass.

11. A method of making a multiwell plate comprising the steps of:

providing an upper plate having an array of open ended wells, said upper plate being formed from an organic polymeric material having a predetermined melting temperature, said upper plate further containing a plurality of metallic flecks integrally blended therethrough;

providing a substantially flat transparent lower plate, said lower plate being comprised of an inorganic material;

contacting said upper plate to said lower plate at an interface;

directing a beam of electromagnetic radiation to the upper plate at said interface through said lower plate and thereby heating said upper plate to the melting temperature of said polymeric material;

wherein the organic polymeric material is a silane functional polymer; and, whereby said upper plate and said lower plate are bonded together.

12. The method of claim 11 wherein the silane functional polymer is poly (ethylene-co-trialkoxyvinylsilane).

13. The method of claim 11 wherein the inorganic material is glass.

14. The method of claim 13 wherein the glass is a borosilicate glass.

15. A method of making a multiwell plate comprising the steps of:

providing an upper plate having an array of open ended wells, said upper plate being formed from an organic polymeric material having a predetermined melting temperature;

providing a lower plate, said lower plate comprising an organic polymeric material having a predetermined melting temperature;

providing an infra red radiation absorbing layer in the form of a gasket, a layer on a bottom surface of the upper plate, or a layer on a top surface of the lower plate;

contacting said upper plate to said lower plate, with said infra-red radiation-absorbing layer therebetween; and heating said infra red radiation absorbing layer to the melting temperature of either the polymeric material of the lower plate, the polymeric material of the upper plate, or both; and whereby said upper plate and said lower plate are bonded together.

16. The method of claim 15 wherein said lower plate is transparent to infra red radiation.

17. The method of claim 16 wherein said upper plate is transparent to infra red radiation.

18. The method of claim 15 wherein the upper plate and the lower plate are made from the same organic polymeric material.

19. The method of claim 15 wherein the upper plate and lower plate are made from different organic polymeric materials.

20. The method of claim 15 wherein said infra-red absorbent layer comprises carbon black.

21. The method of claim 15 wherein said infra-red absorbent layer comprises a laser dye.

22. The method of claim 15 wherein said upper and lower plates comprise an infra red transparent material and wherein an infra red radiation absorbing material is applied to a bottom surface of the upper plate to form an infra red radiation absorbing layer on the bottom surface of the upper plate which contacts the lower plate during the contacting step.

23. The method of claim 15 wherein said upper and lower plates comprise an infra red transparent material and wherein an infra red radiation absorbent material is applied to a top surface of said lower plate which contacts the upper plate to form an infra red radiation absorbing layer on the bottom surface of the upper plate during the contacting step.

24. The method of claim 15 further comprising the step of cleaning the upper and lower plates prior to said contacting step.

25. The method of claim 15 further comprising treating a contacting surface of said lower plate, treating a contacting surface of said upper plate, or treating the contacting surface of both upper and lower plates with gamma radiation prior to said contacting step.

26. The method of claim 15 further comprising the step of imparting a reactive coating to an upper surface of said lower plate, prior to said contacting step.

27. A method of making a multiwell plate comprising the steps of:

providing an upper plate having an array of open ended wells, said upper plate being formed from an organic polymeric material having a predetermined melting temperature;

providing a lower plate, said lower plate being comprised of an organic polymeric material having a predetermined melting temperature;

providing an electromagnetic radiation absorbing layer in the form of a gasket between said upper plate and said lower plate;

heating said electromagnetic radiation absorbing layer to the melting temperature of either the polymeric material of the lower plate, the polymeric material of the upper plate, or both; and whereby said upper plate and said lower plate are bonded together.

* * * * *